United States Patent
Agostini et al.

(12) 
(10) Patent No.: US 6,409,999 B2
(45) Date of Patent: Jun. 25, 2002

(54) SYNERGISTICALLY UV-PHOTOPROTECTING BENZOTRIAZOLE-SUBSTITUTED SILICON/CINNAMIC ACID COMPOSITIONS

(75) Inventors: Isabelle Agostini, Chatenay Malabry; Pascal Arnaud, L'Hay les Roses; Sylvie Guillard, Bondy, all of (FR)

(73) Assignee: Societe L'Oreal, Paris (FR)

( * ) Notice: Subject to any disclaimer, the term of this patent is extended or adjusted under 35 U.S.C. 154(b) by 0 days.

(21) Appl. No.: 09/796,636

(22) Filed: Mar. 2, 2001

Related U.S. Application Data

(63) Continuation of application No. PCT/FR00/01696, filed on Jun. 20, 2000.

(30) Foreign Application Priority Data

Jul. 2, 1999 (FR) .............................. 99 08568

(51) Int. Cl.$^7$ .............................. A61K 7/42; A61K 7/44; A61K 7/00
(52) U.S. Cl. .............................. 424/59; 424/60; 424/400; 424/401
(58) Field of Search .............................. 424/59, 60, 400, 424/407

(56) References Cited

U.S. PATENT DOCUMENTS

| | | |
|---|---|---|
| 3,220,972 A | 11/1965 | Lamoreaux |
| 3,697,473 A | 10/1972 | Polmanteer et al. |
| 4,316,033 A | 2/1982 | Ching |
| 4,328,346 A | 5/1982 | Chung et al. |
| 4,340,709 A | 7/1982 | Jeram et al. |
| 5,089,250 A | 2/1992 | Forestier et al. |
| 5,233,040 A | 8/1993 | Raspanti |
| 5,346,691 A | 9/1994 | Raspanti |
| 5,569,451 A | 10/1996 | Richard et al. |
| 5,585,091 A | 12/1996 | Pelzer et al. |
| 5,610,257 A | 3/1997 | Richard et al. |
| 5,618,520 A | 4/1997 | Hansenne et al. |
| 5,643,557 A | 7/1997 | Eteve et al. |
| 5,663,270 A | 9/1997 | Richard et al. |
| 5,695,747 A | 12/1997 | Forestier et al. |
| 5,714,134 A | 2/1998 | Richard et al. |
| 5,753,209 A | 5/1998 | Ascione et al. |
| 5,801,244 A | 9/1998 | Raspanti |
| 5,955,060 A | 9/1999 | Hüglin et al. |
| 5,955,061 A | 9/1999 | Ascione |
| 5,962,452 A | 10/1999 | Hase et al. |
| 5,976,512 A | 11/1999 | Huber |
| 5,980,872 A | 11/1999 | Luther et al. |
| 6,030,629 A | 2/2000 | Hansenne |
| 6,143,282 A | 11/2000 | Hansenne et al. |

FOREIGN PATENT DOCUMENTS

| | | |
|---|---|---|
| DE | 19726184 A1 | 12/1998 |
| EP | 0392883 A | 10/1990 |
| EP | 0517104 A1 | 12/1992 |
| EP | 0518772 A1 | 12/1992 |
| EP | 0518773 A1 | 12/1992 |
| EP | 0570838 A1 | 11/1993 |
| EP | 0660701 A1 | 7/1995 |
| EP | 0669323 A1 | 8/1995 |
| EP | 0708108 A1 | 4/1996 |
| EP | 0711779 | 5/1996 |
| EP | 0771778 | 5/1996 |
| EP | 0742003 | 11/1996 |
| EP | 0775698 A1 | 5/1997 |
| EP | 0796851 A1 | 9/1997 |
| EP | 0835094 A1 | 4/1998 |
| EP | 0860165 A1 | 8/1998 |
| EP | 0863145 A2 | 9/1998 |
| EP | 0878469 A1 | 11/1998 |
| EP | 0893119 | 1/1999 |
| FR | 2416008 A | 10/1979 |
| FR | 2779959 | 12/1999 |
| FR | 2783711 | 3/2000 |
| GB | 2315991 A | 3/1977 |
| GB | 1539625 A | 1/1979 |
| GB | 2013609 B | 8/1979 |
| GB | 2303549 A | 2/1997 |
| WO | 93/04665 A1 | 3/1993 |
| WO | 97/37634 | 10/1997 |
| WO | 99/66896 A | 12/1999 |
| WO | 01/01946 A1 | 1/2001 |

OTHER PUBLICATIONS

Diffey et al, *J. Soc. Cosmet. Chem.*, 40, 127–133 (1989), published by The Society, Detroit, Michigan.

*Primary Examiner*—Shelley A. Dodson
(74) *Attorney, Agent, or Firm*—Burns, Doane, Swecker & Mathis, L.L.P.

(57) ABSTRACT

Topically applicable cosmetic/dermatological compositions suited for improvedly UV-photoprotecting human skin and/or hair against the deleterious effects of ultraviolet irradiation, advantageously oil-in-water emulsions, contain SPF-synergistically enhancing amounts of (a) at least one UV-screening benzotriazole-substituted silicon compound and (b) at least one UV-screening cinnamic acid derivative, formulated into (c) a topically applicable, cosmetically/dermatologically acceptable vehicle, diluent or carrier therefor.

27 Claims, No Drawings

SYNERGISTICALLY UV-PHOTOPROTECTING BENZOTRIAZOLE-SUBSTITUTED SILICON/CINNAMIC ACID COMPOSITIONS

This application claims priority under 35 U.S.C. § 119 FR-99/08568, filed Jul. 2, 1999, and is a continuation of its corresponding PCT/FR00/01696, filed Jun. 20, 2000, both hereby expressly incorporated by reference, which International Application was published by the International Bureau on Jan. 1, 2001, in French, as WO 01/01946.

BACKGROUND OF THE INVENTION

1. Technical Field of the Invention

The present invention relates to novel cosmetic/dermatological compositions for topical application, for the ultraviolet (UV)-photoprotection of human skin and/or hair, comprising (a) at least one silicon compound containing a benzotriazole substituent as a first UV-screening agent, and (b) as a second UV-screening agent, at least one cinnamic acid derivative.

The present invention more especially relates to the aforesaid UV-photoprotecting compositions wherein said first and said second sunscreens are present in such respective amounts as to provide synergistically enhanced activity with respect to the sun protection factors (SPFs) imparted thereto.

2. Description of the Prior Art

It is known to this art that light radiation with wavelengths of from 280 nm to 400 nm promotes tanning of the human epidermis, and that light rays with wavelengths of from 280 to 320 nm, known as UV-B radiation, cause skin burns and erythema which may be harmful to the development of a natural tan; this UV-B radiation should thus be screened from the skin.

It is also known that UV-A rays, with wavelengths of from 320 to 400 nm, which promote tanning of the skin, are liable to induce an adverse change therein, especially in the case of sensitive skin or of skin which is continually exposed to solar radiation. UV-A rays cause, in particular, a loss of elasticity of the skin and the appearance of wrinkles, leading to premature skin aging. UV-A radiation promotes triggering of the erythemal reaction or amplifies this reaction in certain individuals and may even be the source of phototoxic or photoallergic reactions. It is thus desirable to also screen out UV-A radiation.

A wide variety of cosmetic compositions for the sunblock protection (UV-A and/or UV-B) of the skin have to date been proposed.

These antisun/sunscreen compositions are quite often in the form of an emulsion of oil-in-water type (namely, a cosmetically acceptable support comprising a continuous aqueous dispersing phase and a discontinuous oily dispersed phase) which contains, in various concentrations, one or more conventional lipophilic and/or hydrophilic organic screening agents which are capable of selectively absorbing harmful UV radiation. These screening agents (and the amounts thereof) are selected as a function of the desired sun protection factor ((SPF) which is expressed mathematically by the ratio of the irradiation time necessary to attain the erythema-forming threshold with the UV screening agent to the time required to attain the erythema-forming threshold without UV screening agent.

Cosmetic UV-screening agents comprising lipophilic silicone compounds substituted by a benzotriazole functional group and which have good screening properties both in the UV-A radiation range and in the UV-B radiation range are also known to the prior art. They are described in EP-A-0,392,883; EP-A-0,660,701; EP-A-0,708,108; EP-A-0,711,778; EP-A-711,779.

EP-A-0,742,003 and EP-A-0,860,165 describe combining these silicone screening agents bearing benzotriazole functional groups with specific water-soluble screening agents containing a sulfonic function, namely, benzene-1,4-bis(3-methylidene-10-camphorsulfonic acid) or 2-phenylbenzinidazole-5-sulfonic acid and salts thereof, in order to impart a synergistic effect with respect to the sun protection factors thereof. These synergistic screening systems require at least one aqueous phase for dissolving the water-soluble screening agent and a fatty phase for dissolving the silicone screening agent; this substantially reduces the options for the formulation thereof.

EP-A-0,835,094 describes combining these silicone screening agents bearing a benzotriazole functional group with two other lipophilic screening agents, namely, a dibenzoylmethane compound and an alkyl P,p-diphenylacrylate compound. In this instance also, the mandatory presence of these three screening agents complicates their formulation into antisun/sunscreen products.

UV-screening compositions based on silicon derivatives of benzotriazole in dissolved form containing at least one cinnamic derivative in an amount which is sufficient by itself to dissolve said silicone screening agent are described in French patent application No. 98/12042. This '042 application, in particular, describes a formulation example in the form of an oil-in-water emulsion containing 0.5% by weight of stearic acid, 2.5% by weight of stearyl alcohol, 2% by weight of polydimethylsiloxane, 0.22% of acrylic thickening polymer, 0.72% by weight of triethanolamine, 8% by weight of moisturizer, 5% by weight of drometrizole trisiloxane and 10% by weight of 2-ethylhexyl p-methoxycinnamate. It does not describe any synergistic effect on the protection factors with the benzotriazole-substituted silicon compound.

SUMMARY OF THE INVENTION

It has now surprisingly and unexpectedly been determined that immixture, in proportions within well-defined limits, of a UV-screening agent of the benzotriazole/silicon derivative type and of a UV-screening agent of the cinnamic acid derivative type elicits a marked synergistic effect on the sun protection factors provided thereby. Such admixture provides antisun/sunscreen compositions whose sun protection factors are markedly improved, and in all instances considerably superior to those which can be obtained with either one of the screening agents formulated alone.

Too, the specific combinatory admixture of UV-screening agents in accordance with the invention is readily formulated into a very wide range of cosmetic/dermatological supports, i.e., vehicles, diluents or carriers therefor.

Briefly, the present invention features novel cosmetic/dermatological compositions, in particular antisun/sunscreen compositions comprising, formulated into cosmetically/dermatologically acceptable supports therefor:

(i) at least one benzotriazole-substituted silicon compound, as a first UV-screening agent; and (ii) at least one cinnamic acid derivative, as a second UV-screening agent, with the proviso that said first and second UV-screening agents are present in the subject compositions in proportions which provide synergistically enhanced activity on the sun protection factors imparted. The subject compositions are other than oil-in-water emulsions containing 0.5% by weight of stearic acid, 2.5% by weight of stearyl alcohol, 2% by weight of polydimethylsiloxane, 0.22% of acrylic thickening polymer, 0.72% by weight of triethanolamine, 8% by weight of moisturizer, 5% by weight of drometrizole trisiloxane and 10% by weight of 2-ethylhexyl p-methoxycinnamate.

The present invention also features a regime/regimen for protecting the skin and/or the hair against the deleterious effects of ultraviolet radiation, in particular solar radiation.

This invention also features formulating a cinnamic derivative into cosmetic/dermatological compositions suited for photoprotecting the skin and/or the hair against ultraviolet radiation, in particular solar radiation, and comprising at least one UV-screening agent of the benzotriazole/silicon type, to elicit a synergistic effect on the sun protection factors imparted thereto.

DETAILED DESCRIPTION OF BEST MODE AND SPECIFIC/PREFERRED EMBODIMENTS OF THE INVENTION

More particularly according to the present invention, the silicon compounds substituted by a benzotriazole functional group are preferably silanes or siloxanes containing a benzotriazole function, comprising at least one structural unit of formula (1) below:

in which $R_7$ is an optionally halogenated $C_1-C_{10}$ alkyl radical, a phenyl radical, or a trimethylsilyloxy radical; a is an integer ranging from 0 to 3, inclusive; and G is a monovalent radical directly bonded to a silicon atom and having the structural formula (2) below:

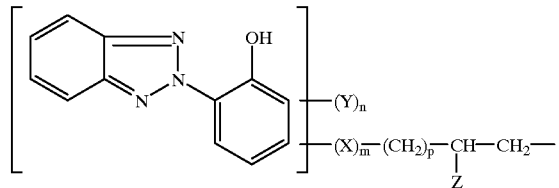

in which the radicals Y, which may be identical or different, are each a $C_1-C_8$ alkyl radical, a halogen atom, or a $C_1-C_4$ alkoxy radical, with the proviso that, in the latter instance, two adjacent radicals Y on the same aromatic ring can together form an alkylidenedioxy radical wherein the alkylidene moiety has 1 or 2 carbon atoms; X is O or NH; Z is hydrogen or a $C_1-C_4$ alkyl radical; n is an integer ranging from 0 to 3, inclusive; m is 0 or 1; and p is an integer ranging from 1 to 10, inclusive.

These compounds are described in particular, in EP-A-0, 392,883; EP-A-0,660,701; EP-A-0,708,108; EP-A-0,711, 778; EP-A-711,779.

The silicon derivatives according to the present invention preferably belong to the general family of benzotriazole silicones which is described, in particular, in EP-A-0,660, 701.

One family of benzotriazole silicones which is particularly preferred according to the present invention is that which includes the compounds corresponding to structural formula (5) or (6) below:

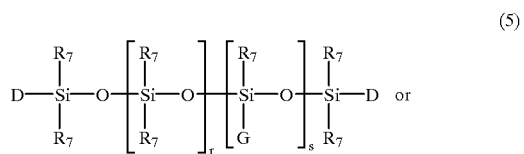

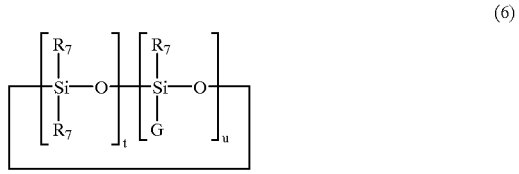

in which the radicals $R_7$, which may be identical or different, are each a $C_1-C_{10}$ alkyl, phenyl, 3,3,3-trifluoropropyl or trimethylsilyloxy radical, at least 80% by number of the radicals $R_7$ being methyl radicals; the radicals D, which may be identical or different, are each a radical $R_7$ or a radical G; r is an integer ranging from 0 to 50, inclusive, and s is an integer ranging from 0 to 20, inclusive, with the proviso that if s=0, at least one of the two radicals D is a radical G; u is an integer ranging from 1 to 6, inclusive, and t is an integer ranging from 0 to 10, inclusive, with the proviso that t+u is equal to or greater than 3; and the radical G has the structural formula (2) above.

As will be seen from formula (2) given above, bonding of the divalent radical $-(X)_m-(CH_2)_p-CH(Z)-CH_2-$ to the benzotriazole function, which thus ensures attachment of said benzotriazole function directly to a silicon atom of the silicone chain, may be at any and all of the available positions of the two aromatic rings of the benzotriazole:

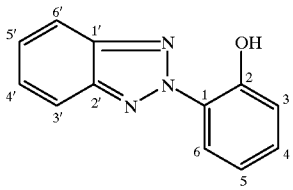

Preferably, this bonding is at position 3, 4, 5 (aromatic ring bearing the hydroxyl function) or 4' (benzene ring adjacent to the triazole ring), and even more preferably is at position 3, 4 or 5. In a more preferred embodiment of the invention, the bonding is at position 3.

Similarly, attachment of the substituent unit or units Y may be at any and all of the other positions available in the benzotriazole. However, preferably, this bonding is at position 3, 4, 4', 5 and/or 6. In a more preferred embodiment of the invention, bonding of the radical Y is at position 5. In formulae (5) and (6) above, the alkyl radicals may be linear or branched and are selected, in particular, from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals $R_7$ according to the invention are methyl, ethyl, propyl, n-butyl, n-octyl and 2-ethylhexyl radicals. Even more preferably, the radicals $R_7$ are all methyl radicals.

Among the compounds of formula (5) or (6) above, preferred are those corresponding to formula (5), namely, diorganosiloxanes containing a short linear chain.

Among the compounds of formula (5) above, preferred are those for which the radicals D are both radicals $R_7$.

Among the linear diorganosiloxanes according to the present invention, more particularly preferred are random derivatives or well-defined block derivatives having at least one, and even more preferably all, of the following characteristics:

D is a radical $R_7$;

$R_7$ is an alkyl radical and even more preferably is methyl;

r ranges from 0 to 15, inclusive;

s ranges from 1 to 10, inclusive;

n is other than zero and preferably is equal to 1, and Y is then a methyl, tert-butyl or $C_1$–$C_4$ alkoxy radical;

Z is hydrogen or methyl;

m=0 or [m=1 and X=0]; and p is equal to 1.

One family of benzotriazole silicones which is particularly suitable according to this invention is that having the structural formula (7) below:

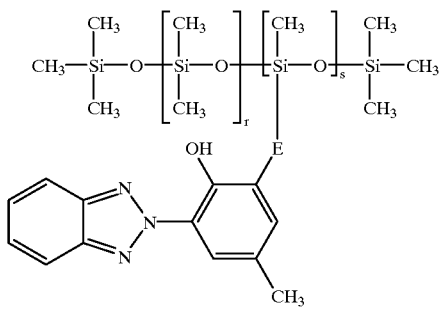

(7)

in which $0 \leq r \leq 10$; $1 \leq s \leq 10$; and E is the divalent radical:

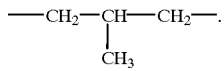

In a particularly preferred embodiment of this invention, the benzotriazole silicone is the compound Drometrizole Trisiloxane (CTFA name) corresponding to the following structural formula:

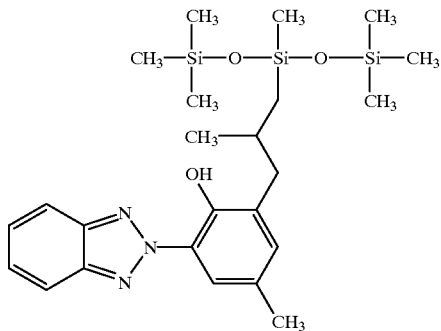

Processes which are suitable for the preparation of the compounds of formulae (1), (5), (6) and (7) above are described, in particular, in U.S. Pat. Nos. 3,220,972, 3,697,473, 4,340,709, 4,316,033 and 4,328,346 and also in EP-A-0,392,883 and EP-A-0,742,003.

The silicon compound substituted by a benzotriazole function is advantageously present in the compositions according to the invention in contents of from 0.1% to 20% by weight, preferably from 0.2% to 15% by weight, still relative to the total weight of the composition.

Exemplary cinnamic acid derivatives according to the present invention include isopentyl 4-methoxycinnamate, 2-ethylhexyl 4-methoxycinnamate, methyl diisopropylcinnamate, isoamyl 4-methoxycinnamate and diethanolamine 4-methoxycinnamate.

Among the cinnamic acid derivatives indicated above, most particularly preferred is 2-ethylhexyl p-methoxycinnamate which is marketed under the trademark "Parsol MCX" by Givaudan; this UV-screening agent has the following structural formula:

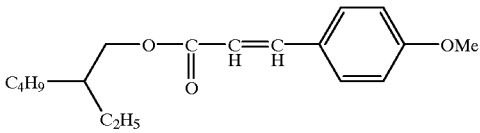

The cinnamic acid derivative(s) of the invention is(are) advantageously present at contents ranging from 0.1% to 20% by weight and preferably from 0.2% to 15% by weight relative to the total weight of the composition.

As indicated above, one essential functional characteristic of the present invention is that the two types of sunscreen should both be present in the final composition in a respective proportion such that a synergistic effect on the protection factor imparted by the resulting combination is obtained in an appreciable, substantial and significant manner.

In addition, and generally, it should be appreciated that the concentrations and ratios of benzotriazole silicon derivative and of cinnamic acid derivative are selected such that the sun protection factor of the final composition is preferably at least 2.

The weight ratio of the cinnamic derivative to the benzotriazole silicon derivative will preferably range from 0.5/6.5 to 6.75/0.25.

The sunscreen cosmetic/dematological compositions according to the invention can of course contain one or more additional hydrophilic or lipophilic sunscreens that are active in the UV-A and/or UV-B range (absorbers) other than the two particular screening agents indicated above. These additional screening agents are advantageously selected from among salicylic derivatives, camphor derivatives; triazine derivatives such as those described in EP-863,145, EP-517,104, EP-570,838, EP-796,851, EP-775,698 and EP-878,469; benzophenone derivatives; dibenzoylmethane derivatives; β,β-diphenylacrylate derivatives; benzimidazole derivatives; p-aminobenzoic acid derivatives; hydrocarbon-based bis(benzotriazolyl-phenol) derivatives such as those described in GB-A-2,303,549, DE-19726184 and EP-A-893,119; compounds comprising at least two benzazolyl groups such as those described in EP-A-0,669,323; and screening polymers and screening silicones such as those described in WO-93/04665.

Exemplary such additional sunscreens that are active in the UV-A and/or UV-B range include:

p-aminobenzoic acid,
oxyethylenated (25 mol) p-aminobenzoate,
2-ethylhexyl p-dimethylaminobenzoate,
N-oxypropylenated ethyl p-aminobenzoate,
glyceryl p-aminobenzoate,
homomenthyl salicylate,
2-ethylhexyl salicylate,
triethanolamine salicylate,
4-isopropylbenzyl salicylate,
4-tert-butyl-4 '-methoxydibenzoylmethane,
4-isopropyldibenzoylmethane,
menthyl anthranilate, 2-ethylhexyl 2-cyano-3,3'-diphenylacrylate,
ethyl 2-cyano-3,3'-diphenylacrylate,
2-phenylbenzimidazole-5-sulfonic acid and salts thereof,
3-(4'-trimethylammonium)benzylidenebornan-2-one methyl sulfate,
2-hydroxy-4-methoxybenzophenone,
2-hydroxy-4-methoxybenzophenone 5-sulfonate,
2,4-dihydroxybenzophenone,
2,2',4,4'-tetrahydroxybenzophenone,
2,2'-dihydroxy-4,4'-dimethoxybenzophenone,
2-hydroxy-4-n-octoxybenzophenone,
2-hydroxy-4-methoxy-4'-methylbenzophenone,
α-(2-oxoborn-3-ylidene)tolyl-4-sulfonic acid and salts thereof,
3-(4'-sulfo)benzylidenebornan-2-one and salts thereof,
3-(4'-methylbenzylidene)-d,1-camphor,
3-benzylidene-d,1-camphor,
benzene-1,4-bis(3-methylidene-10-camphorsulfonic acid) and salts thereof, urocanic acid,
2,4,6-tris [p-(2'-ethylhexyl-1'-oxycarbonyl)anilino]-1,3,5-triazine,
2-[(p-(tert-butylamido)anilino]-4,6-bis [(p-(2'-ethylhexyl-1'-oxycarbonyl)anilino]-1,3,5-triazine,
2,4-bis{[4-(2-ethyl-hexyloxy)]-2-hydroxy]phenyl}-6-(4-methoxyphenyl)-1,3,5-triazine,
N-(2 and 4)-[(2-oxoborn-3-ylidene)methyl]benzyl] acrylamide polymer,
4,4-bis-benzimidazolyl-phenylene-3,3',5,5'-tetrasulfonic acid and salts thereof,
2,2'-methylenebis [6-(2H-benzotriazole-2-yl)-4(1,1,3,3-tetramethylbutyl)phenol], polyorganosiloxanes substituted by a malonate functional group.

The compositions according to the invention may also contain agents for the sunless or artificial tanning and/or browning of the skin (self-tanning agents) such as, for example, dihydroxyacetone (DHA).

The cosmetic/dematological compositions of this invention may also contain pigments or nanopigments (average size of the primary particles: generally ranging from 5 nm to 100 nm, preferably from 10 nm to 50 nm) of coated or uncoated metal oxides, such as, for example, nanopigments of titanium dioxide (amorphous or crystallized in rutile and/or anatase state), of iron oxide, of zinc oxide, of zirconium oxide or of cerium oxide which are all UV-photoprotective agents that are well known per se. Standard coating agents are, moreover, alumina and/or aluminum stearate. Such coated or uncoated metal oxide nanopigments are described, in particular, in EP-A-0,518,772 and EP-A-0,518,773.

The compositions of the present invention may also comprise standard cosmetic additives and adjuvants selected, in particular, from among fatty substances, organic solvents, thickeners, softeners, antioxidants, opacifiers, stabilizers, emollients, hydroxy acids, anti-foaming agents, moisturizers, vitamins, fragrances, preservatives, surfactants, fillers, sequestering agents, propellants, basifying or acidifying agents, dyes, colorants or any other ingredient conventionally employed in cosmetics, in particular for the formulation of antisun/sunscreen compositions as emulsions.

The fatty substances may comprise an oil or a wax or mixtures thereof, and they also comprise fatty acids, fatty alcohols and fatty acid esters. Exemplary oils include animal, plant, mineral or synthetic oils and, in particular, liquid petrolatum, liquid paraffin, volatile or non-volatile silicone oils, isoparaffins, poly-α-olefins, fluoro oils and perfluoro oils. Similarly, exemplary waxes include animal, fossil, plant, mineral or synthetic waxes that are known per se.

Exemplary organic solvents include the lower alcohols and polyols.

The thickeners are advantageously selected from among crosslinked acrylic acid homopolymers and modified or unmodified guar gums and cellulose gums such as hydroxypropylated guar gum, methylhydroxyethylcellulose, hydroxypropylmethylcellulose, or hydroxyethylcellulose.

One skilled in this art will of course take care to select the optional complementary compound or compounds indicated above and/or the amounts thereof such that the advantageous properties, especially the enhanced sunblock effect, intrinsically associated with the binary combination in accordance with the invention are not, or are substantially not, adversely affected by the addition or additions envisaged.

The compositions of the invention may be formulated according to techniques which are well known to this art, in particular those suited for the preparation of emulsions of oil-in-water or water-in-oil type, or, alternatively, anhydrous compositions.

The subject compositions may be, in particular, in simple or complex emulsion form (O/W, W/O, O/W/O or W/O/W), such as a cream, a milk, a lotion, an ointment, a gel or a cream-gel, or in the form of a powder, a solid composition or soft pastes and may optionally be packaged as an aerosol and may be in the form of a foam, mousse, or spray.

When the composition is an emulsion, the aqueous phase thereof may comprise a nonionic vesicular dispersion prepared according to known techniques (Bangham, Standish and Watkins, *J. Mol. Biol.*, 13, 238 (1965), FR-2,315,991 and FR-2,416,008).

The cosmetic compositions of the invention are well suited as compositions for photoprotecting the human epidermis or the hair against the deleterious effects of ultraviolet radiation, as an antisun/sunscreen composition or as a makeup product.

When the cosmetic/dermatological compositions according to the invention are formulated for protecting the human epidermis against UV rays or as an antisun/sunscreen composition, they may be in the form of a suspension or dispersion in solvents or in fatty substances, in the form of a nonionic vesicular dispersion, or, alternatively, in the form of an emulsion, preferably of oil-in-water type, such as a cream or a milk, or in the form of an ointment, a gel, a cream-gel, a stick, soft pastes, an aerosol foam or a spray.

When the cosmetic/dermatological compositions according to the invention are formulated to protect the hair, they may be in the form of a shampoo, a lotion, a gel, an emulsion or a nonionic vesicular dispersion and may constitute, for example, a rinse-out composition to be applied before or after shampooing, before or after dyeing or bleaching, before, during or after permanent-waving or straightening of the hair, a styling or treating lotion or gel, a blow-drying or hair-setting lotion or gel, or a composition for permanent-waving, straightening, dyeing or bleaching the hair.

When the subject compositions are formulated as makeup products for the eyelashes, the eyebrows or the skin, such as an epidermal treatment cream, a foundation, a lipstick, an eyeshadow, a blusher, a mascara or an eyeliner, they may be in solid or pasty, anhydrous or aqueous form, for example oil-in-water or water-in-oil emulsions, nonionic vesicular dispersions or suspensions.

For example, for the antisun/sunscreen formulations in accordance with the invention which have a support of oil-in-water emulsion type, the aqueous phase (in particular comprising the hydrophilic screening agents) generally constitutes from 50% to 95% by weight, preferably from 70% to 90% by weight, relative to the total weight of the overall formulation, the oily phase (in particular comprising the lipophilic screening agents) from 5% to 50% by weight, preferably from 10% to 30% by weight, relative to the total weight of the overall formulation, and the (co)emulsifying agent(s) from 0.5% to 20% by weight, preferably from 2% to 10% by weight, relative to the total weight of the overall formulation.

One particular embodiment of the invention is a care and/or makeup stick for the lips comprising at least one of the compositions described above.

As above indicated, the present invention also features a cosmetic treatment regime/regimen for the skin or the hair to protect same against the damaging effects of UV rays, comprising topically applying an effective amount of a subject cosmetic composition onto the skin or the hair.

In order to further illustrate the present invention and the advantages thereof, the following specific examples are given, it being understood that same are intended only as illustrative and in nowise limitative.

EXAMPLES 1 to 12

| Common support: care stick for the lips | % by weight |
|---|---|
| Microcrystalline wax | 5.00 |
| Glyceryl trihydroxystearate | 5.00 |
| Ozokerite | 3.40 |

-continued

| Common support: care stick for the lips | % by weight |
|---|---|
| Polyglycerolated beeswax | 2.10 |
| Acetylated lanolin | 19.45 |
| Lanolin oil | 19.10 |
| Avocado oil | 18.99 |
| Butene/isobutene copolymer | 14.34 |
| Castor oil | 4.81 |
| Ascorbyl palmitate | 0.50 |
| Mixture of tocopherols in soybean oil (50/50) | 0.31 |
| 2-ethylhexyl para-methoxycinnamate (Parsol MCX) | X |
| (*) Drometrizole trisiloxane | Y |
| With X + Y = 7% by weight | |

Drometrizole trisiloxane has the structural formula:

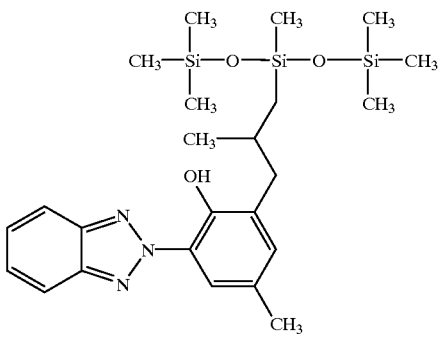

For each of the Examples 1 to 12, the sun protection factor (SPF) associated therewith was determined. This was determined via the in vitro method disclosed by B. L. Diffey et al. in *J. Soc. Cosmet. Chem.*, 40 127-133 (1989). The measurements were carried out using an SPF 290 S model UV-visible spectrophotometer from Optometrics equipped with an integration sphere and a xenon lamp.

Each cosmetic formulation was applied onto a Transpore adhesive tape from 3M adhered to a quartz slide, in the form of a homogeneous and uniform deposit at a rate of 2 mg/cm$^2$.

The compositions of the various formulations studied and the results obtained in terms of average sun protection factor (average of five tests) are reported in the Table below:

TABLE

| Screening agent | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|
| % X | 7 | 6.75 | 6.50 | 6.00 | 5.00 | 4.00 | 3.00 | 2.00 | 1.00 | 0.50 | 0.25 | 0 |
| % Y | 0 | 0.25 | 0.50 | 1.00 | 2.00 | 3.00 | 4.00 | 5.00 | 6.00 | 6.50 | 6.75 | 7 |
| Average SPF ± standard deviation | 9.8 ± 0.3 | 10.6 ± 0.7 | 13.0 ± 0.5 | 13.4 ± 0.7 | 12.3 ± 2.1 | 12.4 ± 2.1 | 12.5 ± 1.8 | 11.4 ± 1.4 | 12.5 ± 2.0 | 11.8 ± 1.7 | 13.0 ± 1.7 | 8.9 ± 0.9 |

These results evidence that a significant synergistic effect was provided by combining the cinnamic derivative and the benzotriazole silicon derivative in weight ratios of the cinnamic derivative to the benzotriazole silicon derivative ranging from 0.50/6.50 to 6.75/0.25.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological composition suited for improvedly UV-photoprotecting human skin and/or hair against the deleterious effects of ultraviolet irradiation, comprising SPF-synergistically enhancing amounts of (a) at least one UV-screening benzotriazole-substituted silicon compound and (b) at least one UV-screening cinnamic acid derivative, formulated into (c) a topically applicable, cosmetically/dermatologically acceptable vehicle, diluent or carrier therefor.

2. The cosmetic/dermatological UV-photoprotecting composition as defined by claim 1, said at least one UV-screening benzotriazole-substituted silicon compound (a) comprising a silane and/or polyorganosiloxane containing at least one structural unit having the formula (1):

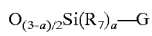 (1)

in which $R_7$ is an optionally halogenated $C_1$–$C_{10}$ alkyl radical, a phenyl radical, or a trimethylsilyloxy radical; a is an integer ranging from 0 to 3, inclusive; and G is a monovalent radical directly bonded to a silicon atom and having the structural formula (2):

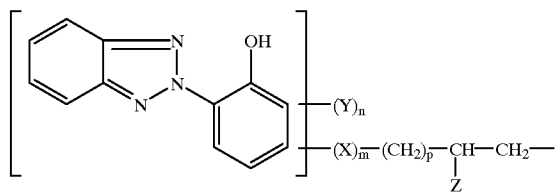 (2)

in which the radicals Y, which may be identical or different, are each a $C_1$–$C_8$ alkyl radical, a halogen atom, or a $C_1$–$C_4$ alkoxy radical, with the proviso that, in the latter instance, two adjacent radicals Y on the same aromatic ring can together form an alkylidenedioxy radical wherein the alkylidene moiety has 1 or 2 carbon atoms; X is O or NH; Z is hydrogen or a $C_1$–$C_4$ alkyl radical; n is an integer ranging from 0 to 3, inclusive; m is 0 or 1; and p is an integer ranging from 1 to 10, inclusive.

3. The cosmetic/dermatological UV-photoprotecting composition as defined by claim 2, said at least one UV-screening benzotriazole-substituted silicon compound (a) having either of the structural formulae (5) and (6):

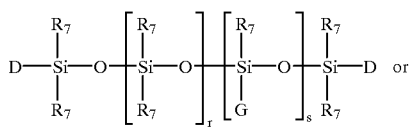 (5)

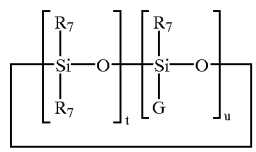 (6)

in which the radicals $R_7$, which may be identical or different, are each a $C_1$–$C_{10}$ alkyl, phenyl, 3,3,3-trifluoropropyl, or trimethylsilyloxy radical, at least 80% by number of the radicals $R_7$ being methyl radicals; the radicals D, which may be identical or different, are each a radical $R_7$ or a radical G; r is an integer ranging from 0 to 50, inclusive, and s is an integer ranging from 0 to 20, inclusive, with the proviso that if s=0, at least one of the two radicals D is a radical G; U is an integer ranging from 1 to 6, inclusive, and t is an integer ranging from 0 to 10, inclusive, with the proviso that t+u is equal to or greater than 3; and the radical G has the structural formula (2).

4. The cosmetic/dermatological UV-photoprotecting composition as defined by claim 1, said at least one UV-screening benzotriazole-substituted silicon compound (a) having the structural formula (7):

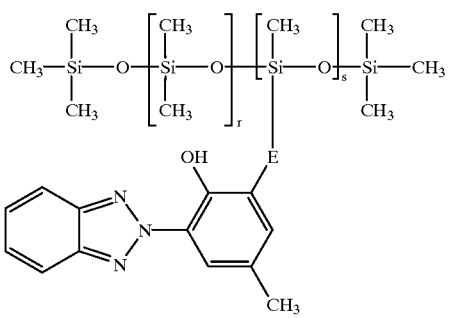 (7)

in which $0 \leq r \leq 10$; $1 \leq s \leq 10$; and E is the divalent radical:

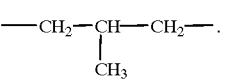

5. The cosmetic/dermatological UV-photoprotecting composition as defined by claim 1, said at least one UV-screening benzotriazole-substituted silicon compound (a) comprising drometrizole trisiloxane having the structural formula:

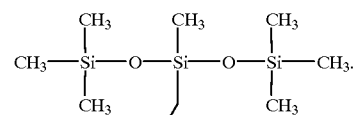

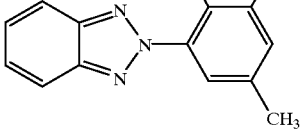

6. The cosmetic/dermatological UV-photoprotecting composition as defined by claim 1, comprising from 0.1% to 20% by weight of said at least one UV-screening benzotriazole-substituted silicon compound (a).

7. The cosmetic/dermatological UV-photoprotecting composition as defined by claim 1, comprising from 0.2% to 15% by weight of said at least one UV-screening benzotriazole-substituted silicon compound (a).

8. The cosmetic/dermatological UV-photoprotecting composition as defined by claim 1, said at least one UV-screening cinnamic acid derivative (b) comprising isopentyl 4-methoxycinnamate, 2-ethylhexyl 4-methoxycinnamate, methyl diisopropylcinnamate, isoamyl 4-methoxycinnamate and/or diethanolamine 4-methoxycinnamate.

9. The cosmetic/dermatological UV-photoprotecting composition as defined by claim 8, said at least one UV-screening cinnamic acid derivative (b) comprising 2-ethylhexyl 4-methoxycinnamate having the structural formula:

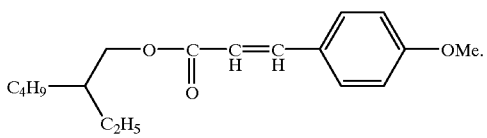

10. The cosmetic/dermatological UV-photoprotecting composition as defined by claim 1, comprising from 0.1% to 20% by weight of said at least one UV-screening cinnamic acid derivative (b).

11. The cosmetic/dermatological UV-photoprotecting composition as defined by claim 1, comprising from 0.2% to 15% by weight of said at least one UV-screening cinnamic acid derivative (b).

12. The cosmetic/dermatological UV-photoprotecting composition as defined by claim 1, having an SPF of at least 2.

13. The cosmetic/dermatological UV-photoprotecting composition as defined by claim 1, the ratio by weight of said at least one cinnamic acid derivative (b) to said at least one benzotriazole-substituted silicon compound (a) ranging from 0.5/6.5 to 6.75/0.25.

14. The cosmetic/dermatological UV-photoprotecting composition as defined by claim 1, further comprising at least one additional hydrophilic or lipophilic organic UV-A and/or UV-B sunscreen.

15. The cosmetic/dermatological UV-photoprotecting composition as defined by claim 14, further comprising at least one salicylic sunscreen, camphor sunscreen, benzophenone sunscreen, dibenzoylmethane sunscreen, triazine sunscreen, β,β-diphenylacrylate sunscreen, p-aminobenzoic acid sunscreen, bis(benzotriazolylphenol) sunscreen, sunscreen comprising at least two benzazolyl functional groups, sunscreen polymer and/or sunscreen silicone other than one benzotriazole-substituted.

16. The cosmetic/dermatological UV-photoprotecting composition as defined by claim 1, further comprising a UV-photoprotecting effective amount of particulates of at least one inorganic pigment or nanopigment.

17. The cosmetic/dermatological UV-photoprotecting composition as defined by claim 16, said at least one pigment or nanopigment comprising titanium dioxide, zinc oxide, iron oxide, zirconium oxide, cerium oxide, or mixture thereof.

18. The cosmetic/dermatological UV-photoprotecting composition as defined by claim 1, further comprising at least one active agent for the artificial tanning and/or browning of human skin.

19. The cosmetic/dermatological UV-photoprotecting composition as defined by claim 1, further comprising at least one cosmetically acceptable adjuvant or additive.

20. The cosmetic/dermatological UV-photoprotecting composition as defined by claim 19, said at least one adjuvant or additive comprising a fat, organic solvent, thickening agent, softener, antioxidant, opacifying agent, stabilizing agent, emollient, hydroxy acid, anti-foaming agent, hydrating agent, vitamin, fragrance, preservative, surfactant, filler, sequestering agent, polymer, propellant, basifying or acidifying agent, dye, colorant, or mixture thereof.

21. The cosmetic/dermatological UV-photoprotecting composition as defined by claim 1, formulated as an emulsion, cream, gel, milk, cream-gel, powder, solid, stick, suspension, mousse, foam, lotion, spray, dispersion, or ointment.

22. The cosmetic/dermatological UV-photoprotecting composition as defined by claim 21, formulated as an oil-in-water emulsion.

23. The cosmetic/dermatological UV-photoprotecting composition as defined by claim 1, comprising a makeup product.

24. The cosmetic/dermatological UV-photoprotecting composition as defined by claim 23, comprising an epidermal treatment cream, a foundation, a lipstick, an eyeshadow, a blusher, a mascara, or an eyeliner.

25. The cosmetic/dermatological UV-photoprotecting composition as defined by claim 21, comprising a shampoo, a hair lacquer, a rinse, a hair styling/treating lotion or gel, or a hair reshaping, straightening, dyeing or bleaching formulation.

26. A regime/regimen for photoprotecting human skin and/or hair against the deleterious effects of UV-irradiation, comprising topically applying thereon a cosmetic/dermatological composition comprising SPF-synergistically enhancing amounts of (a) at least one UV-screening benzotriazole-substituted silicon compound and (b) at least one UV-screening cinnamic acid derivative, formulated into (c) a topically applicable, cosmetically/dermatologically acceptable vehicle, diluent or carrier therefor.

27. The cosmetic/dermatological UV-photoprotecting composition as defined by claim 1, other than an oil-in-water emulsion containing 0.5% by weight of stearic acid, 2.5% by weight of stearyl alcohol, 2% by weight of polydimethylsiloxane, 0.22% of acrylic thickening polymer, 0.72% by weight of triethanolamine, 8% by weight of moisturizer, 5% by weight of drometrizole trisiloxane and 10% by weight of 2-ethylhexyl p-methoxycinnamate.

* * * * *